(12) United States Patent
Lambino

(10) Patent No.: US 7,015,181 B2
(45) Date of Patent: Mar. 21, 2006

(54) REHYDRATABLE PERSONAL CARE COMPOSITIONS

(76) Inventor: Danilo L. Lambino, 43/227 Princes Highway, Kogarah NSW 2217 (AU)

( * ) Notice: Subject to any disclaimer, the term of this patent is extended or adjusted under 35 U.S.C. 154(b) by 37 days.

(21) Appl. No.: 10/795,764

(22) Filed: Mar. 8, 2004

(65) Prior Publication Data
US 2005/0197263 A1    Sep. 8, 2005

(51) Int. Cl.
C11D 3/02       (2006.01)
C11D 3/37       (2006.01)
C11D 3/43       (2006.01)
C11D 17/00      (2006.01)
A61K 7/00       (2006.01)

(52) U.S. Cl. ............ 510/141; 510/121; 510/145; 510/151; 510/403; 510/432; 510/445; 510/470; 510/475; 510/507; 424/401; 424/70.11

(58) Field of Classification Search ........ 510/121, 510/141, 145, 151, 403, 432, 445, 470, 475, 510/507; 424/401, 70.11
See application file for complete search history.

(56) References Cited

U.S. PATENT DOCUMENTS

| | | | |
|---|---|---|---|
| 4,330,438 A | 5/1982 | Dierassi et al. | |
| 5,607,666 A | 3/1997 | Masson et al. | |
| 5,763,500 A | 6/1998 | Roulier et al. | |
| 5,900,241 A | 5/1999 | Roulier et al. | |
| 5,980,971 A | 11/1999 | Walsh | |
| 6,045,814 A | 4/2000 | Roulier et al. | |
| 6,204,230 B1 * | 3/2001 | Taylor et al. | ............... 510/131 |

FOREIGN PATENT DOCUMENTS

| | | |
|---|---|---|
| DE | 4214480 | 11/1993 |
| EP | 1 240 828 A1 | 9/2002 |
| GB | 2 384 705 A | 8/2003 |
| WO | WO 95/05939 A1 | 3/1995 |

OTHER PUBLICATIONS

European Search Report EP05 25 1343 Dated Jul. 18, 2005.

* cited by examiner

Primary Examiner—Brian P. Mruk
(74) Attorney, Agent, or Firm—Erin M. Harriman

(57) ABSTRACT

A rehydratable personal care composition including: from about 1 to about 20 percent water, from about 1 to about 20 percent organic solvent, from about 0.5 to about 50 percent gelling agent, and from about 0.1 to about 5 percent gelling cation, based on the total weight of the composition is disclosed.

9 Claims, No Drawings

REHYDRATABLE PERSONAL CARE COMPOSITIONS

BACKGROUND OF THE INVENTION

1. Field of the Invention

The present invention relates to rehydratable personal care compositions. The rehydratable personal care compositions may be useful as cleansers for skin and/or hair. The compositions may also be useful for delivering benefit agents to the skin and/or hair.

2. Description of the Prior Art

The majority of personal care cleansing products in the market today are sold as liquid products. While widely used, liquid products have disadvantages in terms of storage, packaging, the degree of preservation required, and convenience of use.

Liquid cleansing products typically are sold in bottles. The cost of the bottle frequently contributes significantly to the overall cost of the product. There is a need for a product that provides the same personal care benefits as a liquid product, but doesn't require a bottle for packaging.

Liquid cleansing products usually comprise a substantial amount of water in the formula. The products therefore are susceptible to microbial growth and require preservation. Finding a preservative that is useful in many application areas can be a difficult task. There is a need for a product that provides the same personal care benefits as a liquid product, but doesn't require preservatives to control microbial growth.

Liquid personal care products can be difficult to use in terms of controlling dosage and delivery of the product. There is a need for a product that provides the same personal care benefits as a liquid product, but isn't a liquid.

Patent Cooperation Treaty patent application number WO 9505939 discloses substantially dry, rehydratable, water-dispersible, gel-forming, porous hydrocolloid microparticulates. The microparticulates contain internally or internally and externally at least one water-soluble, non-gelling, hydration enhancing hydrocolloid. The patent also discloses processes and intermediates for the hydrocolloid microparticulates preparation, and their uses.

U.S. Pat. No. 5,980,971 discloses a method for manufacturing dry instantly rehydratable bean paste. The bean paste is rehydrated to a food product having the appearance and organoleptic texture of canned or conventionally prepared Mexican style refried beans.

European Patent number EP1240828 discloses a consumable, viscoelastic, and stringy composition. The composition is freeze-dried, and rehydratable. The composition comprises imitation cheese, pectin, a swellable material, and a soluble calcium salt. The product is suitable for cheese fillings, gratin toppings, pizza toppings, and snacks.

Co-pending U.S. patent application Ser. No. 10/390,095 filed Mar. 17, 2003, the disclosure of which is hereby incorporated by reference, discloses the use of absorbent materials to swell and expand a cleansing implement. The absorbent materials may be blended with cleansers or actives.

Despite the disclosure of the prior art, it is difficult to get uniform distribution of actives or cleansers in dry materials when they are dry blended. Accordingly, there remains a need for rehydratable personal care compositions that do not require bottles as packaging, do not require preservatives, and are easy to control dosage and delivery.

SUMMARY OF THE INVENTION

The present invention provides a rehydratable personal care composition including from about 1 to about 20 percent water, from about 1 to about 20 percent organic solvent, from about 0.5 to about 50 percent gelling agent, and from about 0.1 to about 5 percent gelling cation, based on the total weight of the composition.

DETAILED DESCRIPTION OF PREFERRED EMBODIMENTS

The compositions of the present invention are rehydratable. As used herein, rehydratable means that the compositions were first prepared as liquid compositions, then dried into solid compositions that readily absorb water and rehydrate. The compositions of the invention may be rehydrated into liquids, gels, or semi-solids.

The liquid compositions from which the rehydratable compositions of the present invention originate typically contain from about 0 to about 95 percent and preferably from about 10 to about 50 percent by weight water, based on the total weight of the liquid composition. The liquid compositions generally contain from about 0 to about 50 percent and preferably from about 0 to about 5 percent by weight organic solvent, based on the total weight of the liquid composition. The liquid compositions contain from about 0.2 to about 10 percent and preferably from about 0.5 to about 5 percent by weight gelling agent, based on the total weight of the liquid composition. A chelating agent may be added to the liquid composition. The amount of chelating agent may range from about 0 to about 2 percent by weight, based on the total weight of the liquid composition.

If the rehydratable composition of the present invention is intended for use as a cleanser, at least one surfactant is added to the liquid composition from which the composition of the invention originates. The amount of surfactant in the liquid composition may range from about 1 to about 50 percent and preferably from about 1 to about 20 percent by weight, based on the total weight of the liquid composition. The liquid composition may further include from about 0 to about 10 percent and preferably form about 0 to about 1 percent by weight, based on the total weight of the composition of a preservative.

If the rehydratable composition of the present invention is intended for use in delivering active ingredients to the skin or hair, at least active ingredient is added to the liquid composition from which the composition of the invention originates. The amount of active ingredient in the liquid composition may range from about 0.1 to about 10 percent and preferably from about 1 to about 5 percent by weight, based on the total weight of the liquid composition.

The liquid composition is dried to generate the rehydratable compositions of the present invention. The liquid composition may be dried by conventional methods. Suitable drying methods include fluidized bed drying, vacuum flash drying, freeze-drying, and ambient temperature and humidity air-drying.

To increase the rate of rehydration (for instantaneous gelation) the dried material may be granulated to increase surface area in contact with water. The dehydrated granules may be used directly as a powder cleanser or added to tap water to make liquid bath or shampoo gels. The dried and granulated powder cleansers may be pouched in an apertured film to control the rate of delivery, improve foaming, and provide a cleansing product and cleansing implement all in one.

The rehydratable compositions of the present invention typically contain from about 0 to about 50 percent and preferably from about 1 to about 20 percent by weight water, based on the total weight of the rehydratable composition. The rehydratable compositions generally contain from about 0 to about 50 percent and preferably from about 1 to about 10 percent by weight organic solvent, based on the total weight of the rehydratable composition. The rehydratable compositions contain from about 0.5 to about 75 percent and preferably from about 1 to about 50 percent by weight gelling agent, based on the total weight of the rehydratable composition. If a chelating agent is present in the rehydratable composition, the amount of chelating agent may range from about 0 to about 5 percent, preferably from about 0 to about 2 percent by weight, based on the total weight of the rehydratable composition.

When surfactants are utilized in the rehydratable composition of the present invention, the amount of surfactant in the rehydratale composition may range from about 1 to about 95 percent and preferably from about 25 to about 75 percent by weight, based on the total weight of the rehydratable composition.

When active ingredients for the skin or hair are utilized in the rehydratable compositions of the present invention, the amount of active ingredient in the rehydratable composition may range from about 0.1 to about 20 percent and preferably from about 1 to about 10 percent by weight, based on the total weight of the rehydratable composition.

Suitable gelling agents for use in the present invention include, but are not limited to, natural polymers including those of plant origin examples of which include Karaya gum, Tragacanth gum, Gum arabic, and Gum Ghatti; seed extracts including Guar gum, Locust bean gum, Quince seed, and Psyllium Seed; seaweed extracts such as Carrageenan, alginates, and agar; fruit extracts (pectins); and starches; those of microbial origin including Xanthan gum, Gellan gum, and Dextran; and those of animal origin including Casein, Gelatin, Keratin, and Shellac.

Modified natural polymers are also useful as gelling agents in the present invention. Suitable modified natural polymers include, but are not limited to, cellulose derivatives such as hydroxypropylcellulose, hydroxyethylcellulose and the like; And Guar derivatives such as hydroxypropyl guar.

Synthetic polymers are also useful as gelling agents in the present invention. Suitable synthetic polymers include, but are not limited to, acrylic acid polymers, Polyacrylamides, and alkylene/alkylene oxide polymers.

Inorganic materials such as clays and amorphous silicon dioxides (silica) are also useful as gelling agents in the present invention.

Suitable organic solvents for use in the compositions of the present invention include, but are not limited to, water soluble liquid polyols selected from the group comprising glycerine, propylene glycol, hexylene glycol, butylene glycol, dipropylene glycol, and mixtures thereof; polyalkylene glycols of the formula: $HO-(R''O)_b-H$, wherein R" is an alkylene group having from about 2 to about 3 carbon atoms and b is an integer of from about 2 to about 10; polyethylene glycol ethers of methyl glucose of formula $CH_3-C_6H_{10}O_5-(OCH_2CH_2)_c-OH$, wherein c is an integer from about 5 to about 25; urea; and mixtures thereof.

Suitable gelling cations for use in the compositions of the present invention include, but are not limited to, ethylenediaminetetraacetic acid, calcium chloride, and potassium chloride. The amount of gelling cation may range from about 0.1 to about 10, and preferably from about 0.1 to about 5 percent by weight, based on the total weight of the composition.

Suitable active ingredients for use in the compositions of the present invention include, but are not limited to, cleansers, skin care actives, moisturizers, and the like. As used herein, the term "skin care actives" refers to medicinal and cosmetic agents, which are dispersable in water, and which are used to topically treat the skin. Typical cosmetic agents useful in the present invention include but are not limited to humectants, emollients, and vitamins. Typical medicinal agents useful in the present invention include but are not limited to oatmeal, bicarbonate of soda, colloidal oatmeal, oilated colloidal bath treatment, surfactant based colloidal oatmeal cleanser, other cleanser systems, anti acne agents, anti aging agents, soy powder, herbal medicines and combinations thereof.

Suitable surfactants for use in the compositions of the present invention include, but are not limited to, anionic, nonionic, cationic, and amphoteric lathering surfactants. Nonlimiting examples of anionic lathering surfactants include those selected from the group consisting of sarcosinates, sulfates, isethionates, taurates, phosphates, lactylates, and glutamates. Specific examples include, but are not limited to, those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Nonlimiting examples of nonionic lathering surfactants include those selected from the group consisting of alkyl glucosides, alkyl polyglucosides, polyhydroxy fatty acid amides, alkoxylated fatty acid esters, lathering sucrose esters, amine oxides, and mixtures thereof. Specific examples include, but are not limited to, nonionic surfactants to those selected form the group consisting of C8–C14 glucose amides, C8–C14 alkyl polyglucosides, sucrose cocoate, sucrose laurate, lauramine oxide, cocoamine oxide, and mixtures thereof.

Nonlimiting examples of amphoteric lathering surfactants (which also includes zwitterionic lathering surfactants) are those selected from the group consisting of betaines, sultaines, hydroxysultaines, alkyliminoacetates, iminodialkanoates, aminoalkanoates, and mixtures thereof.

Nonlimiting examples of amphoteric surfactants of the present invention include disodium lauroamphodiacetate, sodium lauroamphoacetate, cetyl dimethyl betaine, cocoamidopropyl betaine, cocoamidopropyl hydroxy sultaine, and mixtures thereof.

Several examples are set forth below to further illustrate the nature of the invention and the manner of carrying it out. However, the invention should not be considered as being limited to the details thereof.

EXAMPLE 1

The following materials were used to make a liquid composition: 91.5 g purified water, 1.5 g GENUGEL LC5 Kappa Carageenan gelling agent, 1.0 g potassium chloride gelling cation, 2.5 g AMISOFT CS-11 sodium cocoyl glutamate surfactant, 1.25 g PLANTAREN 1200 UP lauryl glucoside surfactant, 1.25 g EMPIGEN CDL30/J sodium lauroamphoacetate surfactant, and 1.0 g Phenoxyethanol.

The liquid sample was prepared as follows:

The water was added to a main vessel. GENUGEL LC5 was slowly added to the water and mixed until fully dispersed. The temperature was ramped up to 70–90° C. and mixing was continued until a clear liquid was formed. Potassium chloride was predissolved as a 10% aqueous solution, added to the vessel, and mixed for 5 minutes. The surfactants were added to the vessel in the order above. The batch was cooled to 65° C. and then Phenoxyethanol was added.

The rehydratable composition of the present invention was prepared as follows:

the batch was poured into trays to form a 2 mm–3 mm thick layer of film, the film was dried in 103–105° C. oven for 2 hours or until dry, the dried film was scraped out of the trays and granulated in a coulton granulator to make powders from 5 um to 500 um.

EXAMPLE 2

The following materials were used to make a liquid composition: 92.7 g purified water, 1.5 g KELCOGEL F gellan gum gelling agent, 0.3 g EDETA BD ethylenediaminetetraacetic acid gelling cation, 2.5 g AMISOFT CS-11 sodium cocoyl glutamate surfactant, 1.25 g PLANTAREN 1200 UP lauryl glucoside surfactant, 1.25 g EMPIGEN CDL30/J sodium lauroamphoacetate surfactant, and 0.5 g Phenoxyethanol.

The liquid sample was prepared as follows:

The water was added to a main vessel. KELCOGEL F was slowly added to the water and mixed until fully dispersed. The temperature was ramped up to 70–90° C. and mixing was continued until a clear liquid was formed. EDETA BD was predissolved as a 10% aqueous solution, added to the vessel, and mixed for 5 minutes. The surfactants were added to the vessel in the order above. The batch was cooled to 65° C. and then Phenoxyethanol was added.

The rehydratable composition of the present invention was prepared as follows:

the batch was poured into trays to form a 2 mm–3 mm thick layer of film, the film was dried in 103–105° C. oven for 2 hours or until dry, the dried film was scraped out of the trays and granulated in a coulton granulator to make powders from 5 um to 500 um.

EXAMPLE 3

The following materials were used to make a liquid composition: 71.98 g purified water, 0.8 g KELCOGEL F gellan gum gelling agent, 0.5 g calcium chloride gelling cation, 12.39 g TEXAPON N70T sodium laureth sulfate surfactant, 4.43 g TEGOBETAINE L7 cocamidopropyl betaine surfactant, 9.9 g propylene glycol humectant, and 1.0 g Phenoxyethanol.

The liquid sample was prepared as follows:

The water was added to a main vessel. In a separate vessel, the KELCOGEL F and propylene glycol were mixed and then the mixture was dispersed into the water in the main vessel. The temperature was ramped up to 70–90° C. and mixing was continued until a clear liquid was formed. Calcium chloride was predissolved as a 10% aqueous solution, added to the vessel, and mixed for 5 minutes. The surfactants were added to the vessel in the order above. The batch was cooled to 65° C. and then Phenoxyethanol was added.

The rehydratable composition of the present invention was prepared as follows:

the batch was poured into trays to form a 2 mm–3 mm thick layer of film, the film was dried in 103–105° C. oven for 2 hours or until dry, the dried film was scraped out of the trays and granulated in a coulton granulator to make powders from 5 um to 500 um.

EXAMPLE 4

The following materials were used to make a liquid composition: 80.56 g purified water, 1.0 g GENUGEL LC5 Kappa Carageenan gelling agent, 0.2 g EDETA BD ethylenediaminetetraacetic acid gelling cation, 3.86 g EMPICOL ESC70/AU sodium laureth sulfate surfactant, 6.3 g ATLAS G 4280 cocamidopropyl betaine surfactant, 2.08 g EMPIGEN CDL30J sodium lauroamphoacetate surfactant, 3.0 g PLANTAREN 1200 lauryl glucoside surfactant, 1.0 g AMISOFT CS11 sodium cocoylglutamate surfactant, 1.0 potassium chloride gelling cation, and 1.0 g Phenoxyethanol.

The liquid sample was prepared as follows:

The water was added to a main vessel. GENUGEL LC5 was slowly added to the water and mixed until fully dispersed. The temperature was ramped up to 70–90° C. and mixing was continued until a clear liquid was formed. EDETA BD was predissolved as a 10% aqueous solution, added to the vessel, and mixed for 5 minutes. The surfactants were added to the vessel in the order above. The batch was cooled to 65° C. and then Phenoxyethanol was added.

The rehydratable composition of the present invention was prepared as follows:

the batch was poured into trays to form a 2 mm–3 mm thick layer of film, the film was dried in 103–105° C. oven for 2 hours or until dry, the dried film was scraped out of the trays and granulated in a coulton granulator to make powders from 5 um to 500 um.

EXAMPLE 5

The following materials were used to make a liquid composition: 89.7 g purified water, 1.5 g KELCOGEL F gellan gum gelling agent, 0.3 g VERSENE NA ethylenediaminetetraacetic acid gelling cation, 2.5 g AMISOFT CS-11 sodium cocoyl glutamate surfactant, 1.25 g PLANTAREN 1200 UP lauryl glucoside surfactant, 1.25 g EMPIGEN CDL30/J sodium lauroamphoacetate surfactant, 3.0 g DERMACARE MAP L213K monolaureth phosphate surfactant, and 0.5 g Phenoxyethanol.

The liquid sample was prepared as follows:

The water was added to a main vessel. KELCOGEL F was slowly added to the water and mixed until fully dispersed. The temperature was ramped up to 70–90° C. and mixing was continued until a clear liquid was formed. VERSENE NA was predissolved as a 10% aqueous solution, added to the vessel, and mixed for 5 minutes. The surfactants were added to the vessel in the order above. The batch was cooled to 65° C. and then Phenoxyethanol was added.

The rehydratable composition of the present invention was prepared as follows:

the batch was poured into trays to form a 2 mm–3 mm thick layer of film, the film was dried in 103–105° C. oven for 2 hours or until dry, the dried film was scraped out of the trays and granulated in a coulton granulator to make powders from 5 um to 500 um.

EXAMPLE 6

The following materials were used to make a liquid composition: 85.2 g purified water, 3.0 g AGAR R100 gelling agent, 0.3 g VERSENE NA ethylenediaminetetraacetic acid gelling cation, 5.0 g AMISOFT CS-11 sodium cocoyl glutamate surfactant, 1.25 g PLANTAREN 1200 UP lauryl glucoside surfactant, 1.25 g EMPIGEN CDL30/J sodium lauroamphoacetate surfactant, 3.0 g DERMACARE MAP L213K monolaureth phosphate surfactant, 0.5 g TEXAPON N70T sodium laureth sulfate surfactant, and 0.5 g Phenoxyethanol.

The liquid sample was prepared as follows: The water was added to a main vessel. The AGAR R100 was slowly added to the water and mixed until fully dispersed. The temperature was ramped up to 70–90° C. and mixing was continued until a clear liquid was formed. VERSENE NA was predissolved as a 10% aqueous solution, added to the vessel, and mixed for 5 minutes. The surfactants were added to the vessel in the order above. The batch was cooled to 65° C. and then Phenoxyethanol was added.

The rehydratable composition of the present invention was prepared as follows:

the batch was poured into trays to form a 2 mm–3 mm thick layer of film, the film was dried in 103–105° C. oven for 2 hours or until dry, the dried film was scraped out of the trays and granulated in a coulton granulator to make powders from 5 um to 500 um.

EXAMPLE 7

The following materials were used to make a liquid composition: 89.7 g purified water, 1.5 g CARBOPOL ULTREZ 21 gelling agent, 0.3 g VERSENE NA ethylenediaminetetraacetic acid gelling cation, 2.5 g AMISOFT CS-11 sodium cocoyl glutamate surfactant, 1.25 g PLANTAREN 1200 UP lauryl glucoside surfactant, 1.25 g EMPIGEN CDL30/J sodium lauroamphoacetate surfactant, 3.0 g DERMACARE MAP L213K monolaureth phosphate surfactant, and 0.5 g Phenoxyethanol.

The liquid sample was prepared as follows:

The water was added to a main vessel. The CARBOPOL was slowly added to the water and mixed until fully dispersed. The temperature was ramped up to 70–90° C. and mixing was continued until a clear liquid was formed. VERSENE NA was predissolved as a 10% aqueous solution, added to the vessel, and mixed for 5 minutes. The surfactants were added to the vessel in the order above. The batch was cooled to 65° C. and then Phenoxyethanol was added.

The rehydratable composition of the present invention was prepared as follows:

the batch was poured into trays to form a 2 mm–3 mm thick layer of film, the film was dried in 103–105° C. oven for 2 hours or until dry, the dried film was scraped out of the trays and granulated in a coulton granulator to make powders from 5 um to 500 um.

EXAMPLE 8

A polyethylene copolymer apertured film from Tredegar Films Products was used to make a pouch for holding the rehydratable compositions of the present invention. The film had hexagonal shaped apertures. Two 8.5 inch by 8.5 inch sheets of film were placed together. Three edges of the sheets were heat sealed to form a pouch. The pouch was filled with 10 g of rehydratable granules from Example 1 above. The fourth edges of the sheets were the heat sealed to close the pouch.

EXAMPLE 9

An experiment was conducted to dry 2 kg of 50% liquid solution of Example 2 using a Buchi 190 Minispray Drying machine. The drying unit utilized a co-current flow pattern with hot air flowing in the same direction as the spray beam. The inlet hot air temperature was set at 160–170° C. and the outlet air temperature at 81–83° C. The evaporation capacity was 1.5 Kg water per hour. The particle size range of the dried powder was from 5 to 50 microns.

EXAMPLE 10

A freshly made batch of the liquid sample of Example 2 was poured into 70 mm×25 mm×50 mm rubber moulds and allowed to solidify at 22–25° C. at 50% relative humidity. The initial weight of the solidified bar was recorded. The formed bars were then de-hydrated for 5 hours at 105° C. convection drying oven. The dehydrated bars were weighed and then re-hydrated by immersion in purified water up to 24 hours at 22–25° C. Re-hydrated bars were weighed after 5 hours and after 24-hour immersion. The results indicate up to 77% initial weight recovery of the cleansing bar after 24-hour re-hydration.

What is claimed is:

1. A rehydratable personal care composition comprising:
   from about 1 to about 20 percent water,
   from about 1 to about 20 percent organic solvent,
   from about 0.5 to about 50 percent gelling agent, and
   from about 0.1 to about 5 percent gelling cation, based on the total weight of the composition.

2. The composition according to claim 1 wherein the gelling agent is selected from the group consisting of natural polymers, modified natural polymers, synthetic polymers, and inorganic materials.

3. The composition according to claim 2 wherein the natural polymer is selected from the group consisting of Karaya gum, Tragacanth gum, Gum arabic, Gum Ghatti, Guar gum, Locust bean gum, Quince seed, Psyllium Seed, Carrageenan, alginates, agar, pectins, starches, Xanthan gum, Gellan gum, Dextran, Casein, Gelatin, Keratin, and Shellac.

4. The composition according to claim 2 wherein the modified natural polymer is selected from the group consisting of hydroxypropylcellulose, hydroxyethylcellulose, and hydroxypropyl guar.

5. The composition according to claim 2 wherein the synthetic polymer is selected from the group consisting of acrylic acid polymers, Polyacrylamides, and alkylene/alkylene oxide polymers.

6. The composition according to claim 2 wherein the inorganic material is selected from the group consisting of clays and amorphous silicon dioxides.

7. The composition according to claim 1 wherein the organic solvent is selected from the group consisting of glycerine, propylene glycol, hexylene glycol, butylene glycol, dipropylene glycol, and mixtures thereof; polyalkylene glycols of the formula: HO—(R"O)$_b$—H, wherein R"is an alkylene group having from about 2 to about 3 carbon atoms and b is an integer of from about 2 to about 10; polyethylene glycol ethers of methyl glucose of formula CH$_3$—C$_6$H$_{10}$O$_5$—(OCH$_2$CH$_2$)$_c$—OH, wherein c is an integer from about 5 to about 25; urea; and mixtures thereof.

8. The composition according to claim 7 wherein the organic solvent is selected from the group consisting of glycerine, propylene glycol, and dipropylene glycol.

9. The composition according to claim 1 wherein the gelling cation is selected from the group consisting of ethylenediaminetetraacetic acid, calcium chloride, and potassium chloride.

* * * * *